United States Patent [19]
Kester et al.

[11] Patent Number: 5,824,100
[45] Date of Patent: Oct. 20, 1998

[54] KNEE PROSTHESIS WITH INCREASED BALANCE AND REDUCED BEARING STRESS

[75] Inventors: Mark A. Kester, Upper Saddle River, N.J.; Marc G. Weissman, Derby, Conn.

[73] Assignee: Osteonics Corp., Allendale, N.J.

[21] Appl. No.: 741,435

[22] Filed: Oct. 30, 1996

[51] Int. Cl.[6] .................................................. A61F 2/42
[52] U.S. Cl. ........................................................ 623/20
[58] Field of Search ................................. 623/16, 18, 20

[56] References Cited

U.S. PATENT DOCUMENTS

| | | |
|---|---|---|
| 3,869,729 | 3/1975 | Attenborough . |
| 4,249,270 | 2/1981 | Bahler et al. ............................... 623/20 |
| 4,298,992 | 11/1981 | Burstein et al. ........................... 623/20 |
| 4,714,472 | 12/1987 | Averill et al. .............................. 623/20 |
| 4,714,474 | 12/1987 | Brooks, Jr. et al. ....................... 623/20 |
| 4,759,767 | 7/1988 | Lacey ......................................... 623/20 |
| 4,895,571 | 1/1990 | Grundei ..................................... 623/20 |
| 4,944,756 | 7/1990 | Kenna ........................................ 623/20 |
| 4,944,757 | 7/1990 | Martinez et al. .......................... 623/20 |
| 5,330,533 | 7/1994 | Walker ....................................... 623/20 |
| 5,639,279 | 6/1997 | Burkirshaw et al. ..................... 623/20 |

FOREIGN PATENT DOCUMENTS

| | | | |
|---|---|---|---|
| 0 582 514 | 2/1994 | European Pat. Off. ................. | 623/20 |

OTHER PUBLICATIONS

Insall, John N. et al, *Surgery of the Knee,* 2nd ed., 735–736.
Plante–Bordeneuve, P. et al., "Tibial High–Density Polyethylene Wear in Conforming Tibiofemoral Prothesis," *The Journal of Bone and Joint Surgery,* vol. 75–B, No. 4 (Jul., 1993), 630–636.

*Primary Examiner*—Mary Beth Jones
*Attorney, Agent, or Firm*—Arthur Jacob

[57] ABSTRACT

A knee prosthesis in which engagement between the femoral component and the tibial component of the knee prosthesis takes place at a contact area along articular surface areas including complementary medial-lateral surface profile contours having a single medial-lateral articular radius defining an arcuate profile, and anterior-posterior surface profile contours along the femoral component and the tibial component, the anterior-posterior surface profile contour of the femoral component having an essentially constant anterior-posterior articular radius throughout regions of the femoral component which contact the tibial component within a primary range of flexion, the center of the anterior-posterior articular radius being located along a line extending laterally between the medial and lateral attachment points of the collateral ligaments of the knee, such that the contact area along the articular surface areas is maintained at a maximum throughout at least the primary range of flexion for minimizing stresses in the tibial component and better balancing tension in the collateral ligaments during articulation of the knee prosthesis at least within the primary range of flexion, and further including an eminence projecting from the tibial component toward the femoral component, and a follower on the femoral component for engaging the eminence for controlled restraint of the femoral component during a limited portion of the primary range of flexion.

18 Claims, 4 Drawing Sheets

KNEE PROSTHESIS WITH INCREASED BALANCE AND REDUCED BEARING STRESS

The present invention relates generally to prosthetic knee implants and pertains, more specifically, to a knee prosthesis which achieves a better balance in the tension in the collateral ligaments of the knee and in which the contact area between the condylar elements of the femoral component of the knee prosthesis and the bearing member of the tibial component is increased, within a primary range of flexion, to reduce stress in the bearing member during articulation of the knee prosthesis throughout the primary range of flexion.

The long-term performance of a knee prosthesis is dependent, to a very large extent, upon the ability of the tibial bearing member of the knee prosthesis to withstand stresses resulting from loads encountered during articulation of the knee prosthesis. One of the more common materials employed for such tibial bearing members is ultra-high molecular weight polyethylene, while the condylar elements of the femoral component usually are constructed of a biocompatible high strength metal, such as a cobalt chrome alloy. The manner in which a knee prosthesis performs is affected by the tension in the collateral ligaments of the knee during articulation of the knee prosthesis. Most current knee prostheses employ designs which strive to simulate the articulation of the natural knee by attempting to duplicate the geometry of the articular surfaces of the natural knee. Many of these knee protheses have been found to experience relatively high stresses placed upon the tibial bearing member as a result of loads encountered during articulation of the knee prosthesis and difficulties in balancing the tension in the collateral ligaments of the knee for optimum performance. Such high stresses and imbalances in the tension in the collateral ligaments have an adverse effect on performance and reliability, and usually lead to a limited service life.

The present invention departs from current designs which attempt to duplicate the geometry of the articular surfaces of the natural knee and provides articular surface geometry which more closely follows that of the natural knee, enabling better performance with greater reliability and increased longevity as a result of attaining better balance of the tension in the collateral ligaments and improved distribution of the load on the tibial bearing member during articulation of the knee prosthesis. As such, the present invention attains several objects and advantages, some of which are summarized as follows: Provides increased areas of contact between the condylar elements of the femoral component of a knee prosthesis and the bearing member of the tibial component for lowered stress in the material of the bearing member during articulation of the knee prosthesis throughout a primary range of articulation; attains a better balance of the tension in the collateral ligaments of the knee during articulation of the knee prosthesis; enables a higher degree of conformity between the condylar elements and the bearing member for reduced bearing stresses during normal activity; provides simplified configurations enabling component parts to be manufactured with increased ease and reduced cost; provides a knee prosthesis which enables exemplary performance and increased reliability over an extended service life.

The above objects and advantages, as well as further objects and advantages, are attained by the present invention which may be described briefly as an improvement in a knee prosthesis for replacing the natural knee, the knee prosthesis having a femoral component and a tibial component, the tibial component including a bearing member and the femoral component including at least one condylar element for confronting and engaging the bearing member to accomplish articulation of the knee prosthesis throughout a range of flexion, including a primary range of flexion between a hyperextended position and a flexed position, the engagement between the condylar element of the femoral component and the bearing member of the tibial component ordinarily taking place at a contact area along articular surface areas of the condylar element and the bearing member, the improvement comprising: anterior-posterior surface profile contours along the condylar element and the bearing member, the anterior-posterior surface profile contour along the condylar element having an essentially constant anterior-posterior articular radius throughout a region of the condylar element which includes portions of the articular surface area of the condylar element which contact the bearing member during articulation throughout the primary range of flexion, the anterior-posterior articular radius having an origin lying generally along a line extending laterally between the medial and lateral collateral ligament attachment points on the femur of the natural knee. In a further improvement, complementary medial-lateral surface profile contours extend along the articular surface areas, the medial-lateral surface profile contours having a single medial-lateral articular radius defining an arcuate profile common to the medial-lateral surface profile contours such that the contact area along the articular surface areas of the condylar element and the bearing member is maintained at a maximum throughout at least the primary range of flexion for minimizing stresses in the bearing member during articulation within the primary range of flexion.

The invention will be understood more fully, while still further objects and advantages will become apparent, in the following detailed description of a preferred embodiment of the invention illustrated in the accompanying drawing, in which.

Figure 1:
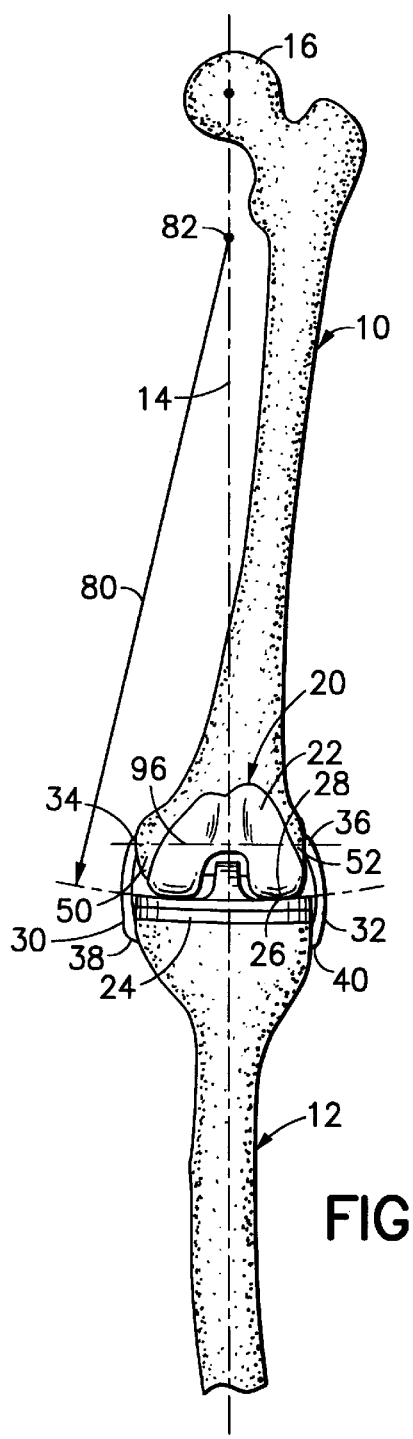
FIG. 1 is a diagrammatic illustration of a prosthetic knee constructed in accordance with the invention and implanted at the joint between the femur and the tibia of a recipient.

Referring now to the drawing, and especially to FIG. 1 thereof, a femur 10 and a tibia 12 extend along a mechanical axis 14 which passes through the center of the head 16 of the natural hip joint. The natural knee joint has been replaced by a knee prosthesis 20 constructed in accordance with the present invention. Knee prosthesis 20 includes a femoral component 22 affixed to the femur 10 and a tibial component 24 affixed to the tibia 12. The femoral component 22 and tibial component 24 provide respective articular surfaces 26 and 28 which engage one another in such a manner as to enable the knee prosthesis 20 to serve as a replacement for the natural knee joint for relative movement of the femur 10 and the tibia 12. As is conventional in such replacements, the natural medial and lateral collateral ligaments 30 and 32 have been preserved and remain attached to the femur 10 at attachment points 34 and 36, and remain attached to the tibia 12 at attachment points 38 and 40.

Figure 2:
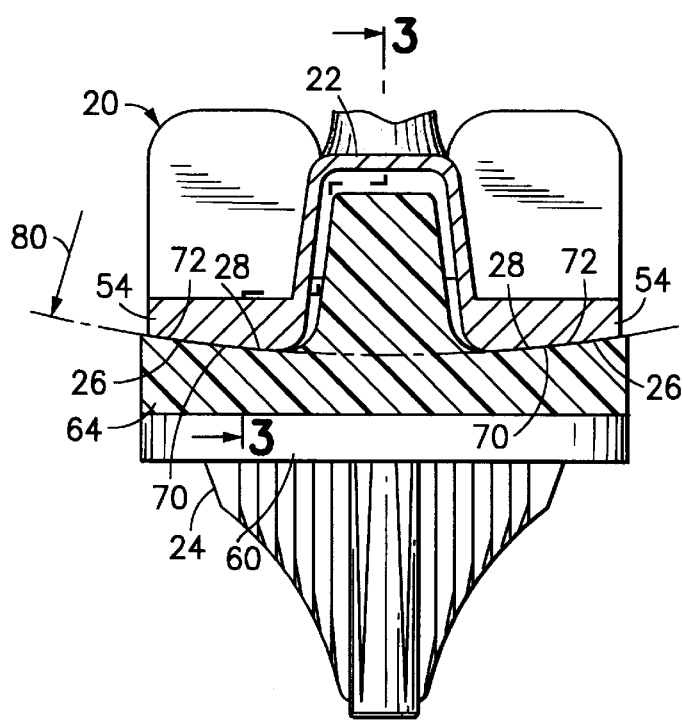
FIG. 2 is an enlarged fragmentary front elevational view, partially sectioned, of component parts of the prosthetic knee.
Figure 3:
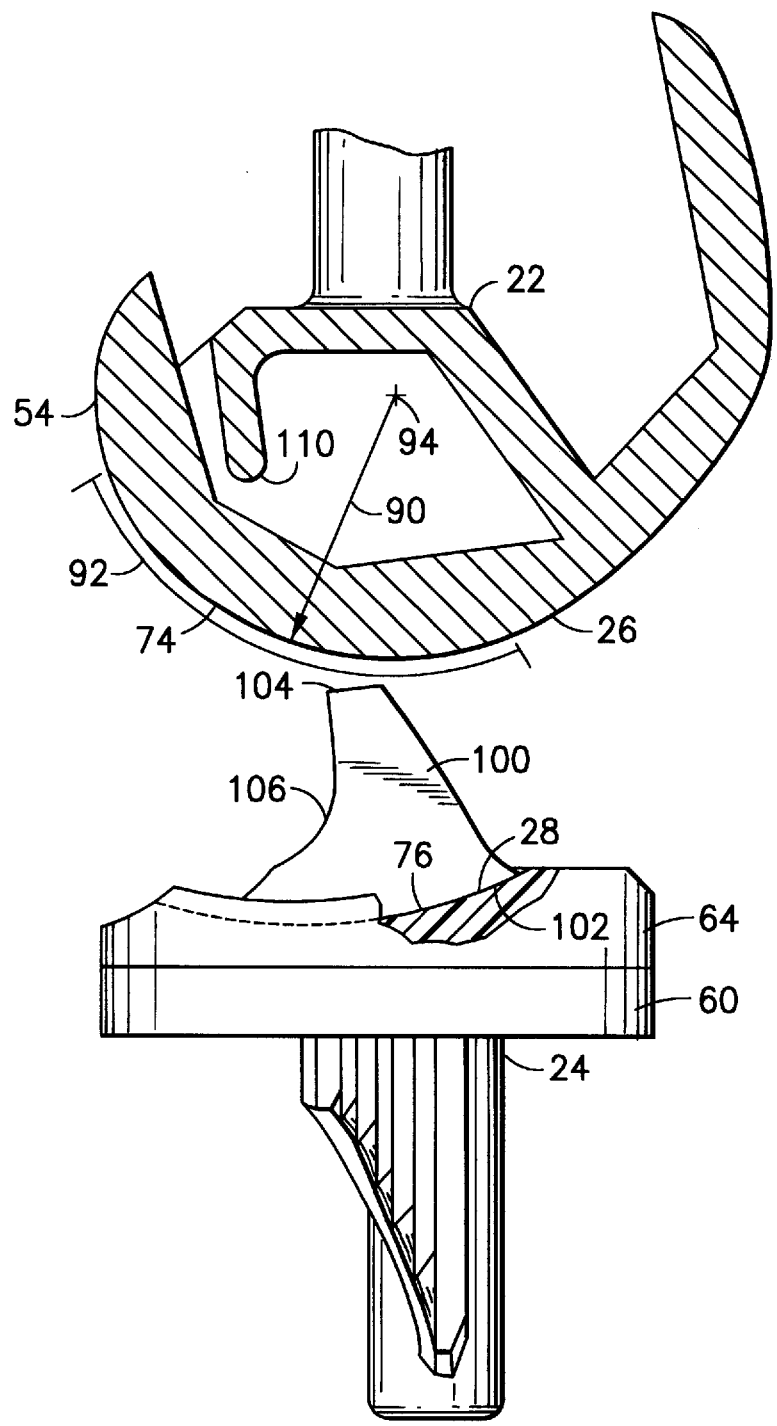
FIG. 3 is a side elevational view, exploded and partially sectioned along line 3—3 of FIG. 2, to show profile contours of the knee prosthesis.

Turning now to FIGS. 2 and 3, as well as to FIG. 1, knee prosthesis 20 is a total knee replacement prosthesis, the femoral component 22 providing a replacement articular surface 26 for each of the medial condyle 50 and the lateral condyle 52 of the femur 10 and the tibial component 24 providing corresponding replacement articular surfaces 28 on the tibia 12. Thus, femoral component 22 is affixed to femur 10 and includes arcuate condylar elements 54 upon which articular surfaces 26 are located. Tibial component 24 is affixed to tibia 12 and includes a platform 60 which supports a bearing member 64 secured in place on the platform 60 and providing articular surfaces 28 for engagement by the respective articular surfaces 26 of the femoral component 22 to enable articulation of the knee prosthesis 20. The arcuate condylar elements 54 preferably are constructed of a high strength biocompatible metal, such as a cobalt chrome alloy, while the preferred material for bearing member 64 is a synthetic polymeric material, such as ultra-high molecular weight polyethylene, which provides the articular surfaces 28 with the appropriate lubricity characteristics for the proper functioning of knee prosthesis 20.

In order to enhance the load-bearing capabilities of knee prosthesis 20, and better enable the accommodation of resulting stresses on the bearing member 64, thereby attaining higher levels of performance as well as increased longevity and greater reliability, contact between the articular surfaces 26 and 28 preferably is maintained along complementary areas of articular surfaces 26 and 28 throughout the range of articulation of the knee prosthesis 20, and especially within a primary range of flexion, as will be set forth in greater detail below. Thus, articular surfaces 26 and 28 are provided with generally complementary profile contours in the medial-lateral plane, or coronal plane, as illustrated by complementary medial-lateral surface profile contours 70 and 72, and are provided with profile contours in the anterior-posterior plane, or sagittal plane, as illustrated by engaging anterior-posterior surface profile contours 74 and 76. In this manner, load is spread over articular surface areas to increase the contact areas between the articular surfaces 26 and 28 and contact stress is reduced, resulting in a reduction in the stresses in the bearing member 64 throughout at least the primary range of flexion.

To this end, the medial-lateral surface profile contours 70 and 72 each follow an arcuate curve having a single articular radius 80 in the medial-lateral plane. The center 82, or origin, of the medial-lateral articular radius 80 lies generally on the mechanical axis 14, between the knee prosthesis 20 and the femoral head 16. Both the medial and lateral articular surfaces 26 lie along the common surface profile contour 70 defined by the medial-lateral articular radius 80. Likewise, the articular surfaces 28 lie along the common medial-lateral surface profile 72, all in much the same manner as described in U.S. Pat. No. 4,714,472.

Figure 4:
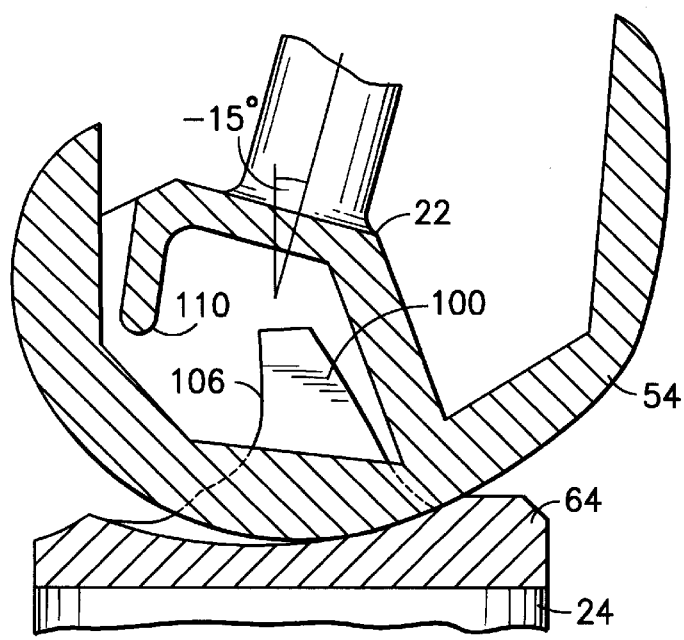
FIGS. 4 through 7 are somewhat diagrammatic, fragmentary cross-sectional views illustrating a range of flexion of the knee prosthesis.
Figure 5:
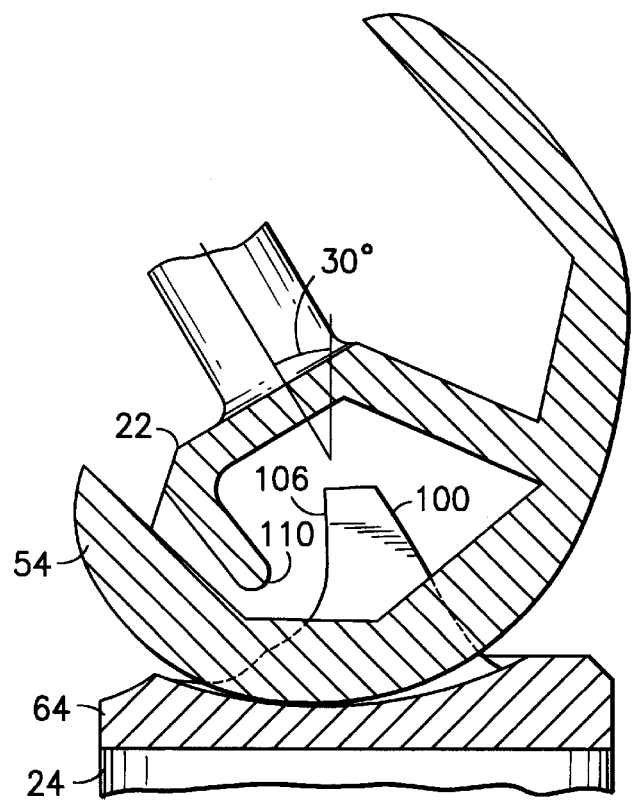
Figure 6:
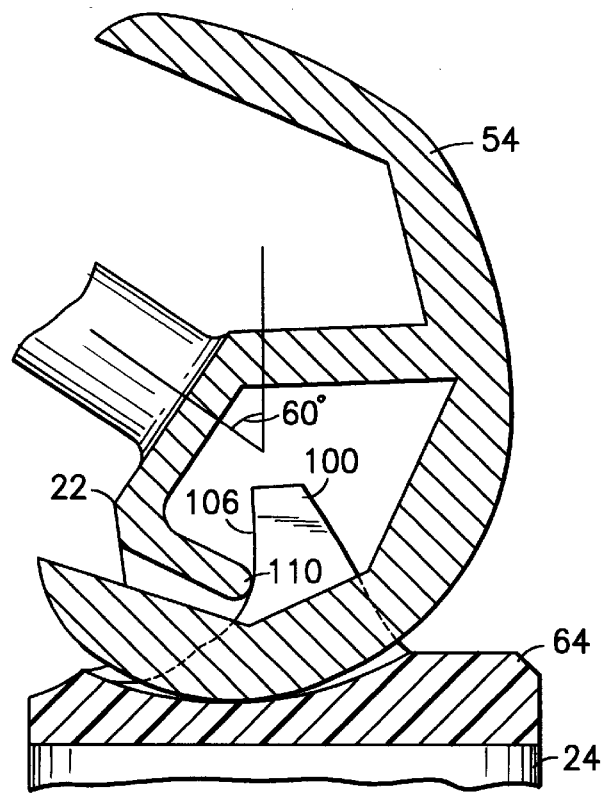
Figure 7:
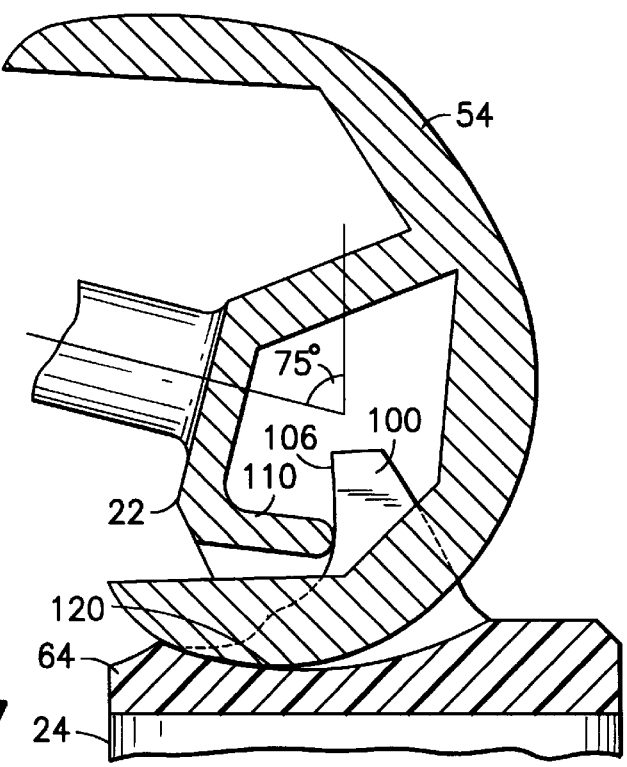

As best seen in FIG. 3, anterior-posterior surface profile contour 74 of knee prosthesis 20 includes an essentially constant anterior-posterior articular radius 90 throughout a region 92 of each condylar element 54. The regions 92 include those portions of the articular surfaces 26 of the condylar elements 54 which contact the bearing member 64 during articulation throughout a portion of the full range of flexion of the knee prosthesis 20, between hyperextension and full flexion, the portion of the full range being the primary range of flexion between a hyperextended position and a flexed position, defining the portion of the full range of flexion within which most normal activities occur. Thus, the primary range of flexion, as depicted in FIGS. 4 through 7, is from a hyperextended position of about −15°, as seen in FIG. 4, to a flexed position of about 75°, as seen in FIG. 7. The anterior-posterior surface profile contour 76 of articular surface 28 of the bearing member 64 enables movement of the femoral component 22 relative to the bearing member 64 of tibial component 24 in anterior-posterior directions during articulation of the knee prosthesis 20.

The center 94, or origin, of the anterior-posterior articular radius 90 preferably is located generally along the laterally-extending line 96 passing through the attachment points 34 and 36 where the medial and lateral collateral ligaments 30 and 32 are attached to the femur 10. Line 96 commonly is referred to as the epicondylar axis. By locating the center 94 of the essentially constant anterior-posterior articular radius 90 generally along the line 96, a better balance is attained in the tension in the collateral ligaments 30 and 32 during articulation of the knee prosthesis 20, resulting in better performance. In addition, the combination of the single medial-lateral articular radius 80 and the essentially constant anterior-posterior articular radius 90 attains a maximum contact area along the complementary articular surface areas of the condylar elements 54 and the bearing member 64 throughout at least the primary range of flexion, thereby minimizing stresses in the bearing member 64 during articulation of the knee prosthesis 20 through the primary range of flexion.

Referring now to FIG. 3, tibial bearing member 64 includes an eminence 100 projecting upwardly, or superiorly, from a lower, or inferior, end 102 adjacent the tibial component 24, toward an upper, or superior, end 104 adjacent the femoral component 22 for reception between the condylar elements 54 of the femoral component 22, and includes a cam surface 106. A follower 110 on the femoral component 22 is located for engagement with the cam surface 106 during a portion of the primary range of flexion of the knee prosthesis 20. As depicted in FIGS. 4 through 7, the cam surface 106 and the follower 110 are arranged such that the follower 110 is disengaged from the cam surface 106 through a first portion of the primary range of flexion of the knee prosthesis 20, the first portion extending from the hyperextended position of about −15°, as seen in FIG. 4, through about 60° of flexion, as illustrated in FIG. 6. Upon engagement of the follower 110 with the cam surface 106, at about 60° of flexion, flexion of the knee prosthesis 20 continues through a second portion of the primary range of flexion until reaching the flexed position of about 75°, as seen in FIG. 7. During flexion of the knee prosthesis 20 through the second portion of the primary range of flexion, the engagement of the follower 110 with the cam surface 106 provides controlled restraint against excessive relative movement between the femoral component 22 and the tibial component 24 in anterior-posterior directions and induces rollback which prolongs a maximum conformity between the complementary areas of articular surfaces 26 and 28 of the condylar elements 54 and the bearing member 64, within the second portion of the primary range, by maintaining contact between the articular surface areas at or near the lowest point 120 of the articular surface 28 of the bearing member 64. In this manner, the controlled restraint provided by the engagement of the follower 110 with the cam surface 106 acts in concert with the single medial-lateral articular radius 80 and the essentially constant anterior-posterior articular radius 90 to attain a further reduction of the stresses encountered in the bearing member 64 during articulation of the knee prosthesis through the second portion of the primary range of flexion. During normal activities which impose higher loads on the knee prosthesis in anterior-posterior directions, such as during stair climbing and rising from or lowering to a seated position, the controlled restraint provided within the second portion of the primary range of flexion assists in managing the stresses encountered in the bearing member 64 for enhanced performance, increased reliability and greater longevity in the knee prosthesis 20.

It will be seen that the present invention attains the objects and advantages summarized above, namely: Provides increased areas of contact between the condylar elements of the femoral component of a knee prosthesis and the bearing member of the tibial component for lowered stress in the material of the bearing member during articulation of the knee prosthesis throughout a primary range of articulation; attains a better balance of the tension in the collateral ligaments of the knee during articulation of the knee prosthesis; enables a higher degree of conformity between the condylar elements and the bearing member for reduced bearing stresses during normal activity; provides simplified configurations enabling component parts to be manufactured with increased ease and reduced cost; provides a knee prosthesis which enables exemplary performance and increased reliability over an extended service life.

It is to be understood that the above detailed description of a preferred embodiment of the invention is provided by way of example only. Various details of design and construction may be modified without departing from the true spirit and scope of the invention, as set forth in the appended claims.

The embodiments of the invention in which an exclusive property or privilege is claimed are defined as follows:

1. In a knee prosthesis for replacing the natural knee, the knee prosthesis having a femoral component and a tibial component, the tibial component including a bearing member and the femoral component including at least one condylar element for confronting and engaging the bearing member to accomplish articulation of the knee prosthesis throughout a range of flexion, including a primary range of flexion between a hyperextended position and a flexed position, the femoral component and the tibial component ordinarily being aligned axially along a mechanical axis passing through the femoral head of the corresponding hip joint and the engagement between the condylar element of the femoral component and the bearing member of the tibial component ordinarily taking place at a contact area along articular surface areas of the condylar element and the bearing member, the improvement comprising:

complementary medial-lateral surface profile contours extending along the articular surface areas, the medial-lateral surface profile contours having a single medial-lateral articular radius defining an arcuate profile common to the medial-lateral surface profile contours; and anterior-posterior surface profile contours along the condylar element and the bearing member, the anterior-posterior surface profile contour along the condylar element having an essentially constant anterior-posterior articular radius throughout the articular surface area of the condylar element which contacts the bearing member during articulation throughout the primary range of flexion, such that the contact area along the articular surface areas of the condylar element and the bearing member is maintained at a maximum throughout at least the primary range of flexion for minimizing stresses in the bearing member during articulation within the primary range of flexion.

2. The improvement of claim 1 wherein the medial-lateral articular radius has an origin lying generally along the mechanical axis.

3. The improvement of claim 1 wherein the anterior-posterior articular radius has an origin lying generally along a line extending laterally between the medial and lateral collateral ligament attachment points on the femur of the natural knee.

4. The improvement of claim 1 wherein the medial-lateral articular radius has an origin lying generally along the mechanical axis, and the anterior-posterior articular radius has an origin lying generally along a line extending laterally between the medial and lateral collateral ligament attachment points on the femur of the natural knee.

5. The improvement of claim 1 wherein the hyperextended position is at about −15° in the range of flexion.

6. The improvement of claim 1 wherein the flexed position is at about 75° in the range of flexion.

7. The improvement of claim 1 wherein the hyperextended position is at about −15° in the range of flexion, and the flexed position is at about 75° in the range of flexion.

8. The improvement of claim 1 including:

an eminence projecting superiorly longitudinally upwardly from an inferior end adjacent the tibial component toward a superior end adjacent the femoral component for reception within the femoral component;

a cam surface on the eminence; and a follower on the femoral component for following the cam surface;

the cam surface and follower being arranged such that the follower is disengaged from the cam surface in a first portion of the primary range of flexion from the hyperextended position through about 60° of flexion, and then is engaged with the cam surface in a second portion of the primary range of flexion from about 60° of flexion to the flexed position to provide controlled restraint against excessive relative movement between the femoral component and the tibial component in anterior-posterior directions within the second portion of the range of flexion.

9. The improvement of claim 8 wherein the hyperextended position is at about −15° in the range of flexion.

10. The improvement of claim 8 wherein the flexed position is at about 75° in the range of flexion.

11. The improvement of claim 8 wherein the hyperextended position is at about −15° in the range of flexion, and the flexed position is at about 75° in the range of flexion.

12. The improvement of claim 11 wherein the medial-lateral articular radius has an origin lying generally along the mechanical axis.

13. The improvement of claim 11 wherein the anterior-posterior articular radius has an origin lying generally along a line extending laterally between the medial and lateral collateral ligament attachment points on the femur of the natural knee.

14. The improvement of claim 11 wherein the medial-lateral articular radius has an origin lying generally along the mechanical axis, and the anterior-posterior articular radius has an origin lying generally along a line extending laterally between the medial and lateral collateral ligament attachment points on the femur of the natural knee.

15. In a knee prosthesis for replacing the natural knee, the knee prosthesis having a femoral component and a tibial component, the tibial component including a bearing member and the femoral component including at least one condylar element for confronting and engaging the bearing member to accomplish articulation of the knee prosthesis throughout a range of flexion, including a primary range of flexion between a hyperextended position and a flexed position, the engagement between the condylar element of the femoral component and the bearing member of the tibial component ordinarily taking place at a contact area along articular surface areas of the condylar element and the bearing member, the improvement comprising:

anterior-posterior surface profile contours along the condylar element and the bearing member, the anterior-posterior surface profile contour along the condylar element having an essentially constant anterior-posterior articular radius throughout the articular surface area of the condylar element which contacts the bearing member during articulation throughout the primary range of flexion, the anterior-posterior articular radius having an origin lying generally along a line extending laterally between the medial and lateral collateral ligament attachment points on the femur of the natural knee.

16. The improvement of claim 15 wherein the hyperextended position is at about −15° in the range of flexion.

17. The improvement of claim 15 wherein the flexed position is at about 75° in the range of flexion.

18. The improvement of claim 15 wherein the hyperextended position is at about −15° in the range of flexion, and the flexed position is at about 75° in the range of flexion.

* * * * *